(12) United States Patent
Pomytkin et al.

(10) Patent No.: US 6,521,665 B1
(45) Date of Patent: Feb. 18, 2003

(54) METHOD OF TREATING INSULIN RESISTANCE

(76) Inventors: Igor Anatolievich Pomytkin, Shkolny bulv., 1B-35 Chernogolovka, Noginsky r-on, 142432 Moskovskaya obl. (RU); Olga Evgenievna Kolesova, ul. 2-aya Peschanaya, 6-82, Moscow, 125252 (RU); Tatiyana Jurievna Ukhanova, ul. 2-aya Peschanaya, 6-82, Moscow, 125252 (RU)

( * ) Notice: Subject to any disclaimer, the term of this patent is extended or adjusted under 35 U.S.C. 154(b) by 0 days.

(21) Appl. No.: 09/914,499

(22) PCT Filed: Mar. 1, 1999

(86) PCT No.: PCT/RU99/00055

§ 371 (c)(1),
(2), (4) Date: Aug. 29, 2001

(87) PCT Pub. No.: WO00/51594

PCT Pub. Date: Sep. 8, 2000

(51) Int. Cl.[7] ............................................. A61K 31/194
(52) U.S. Cl. ....................................................... 514/574
(58) Field of Search ......................................... 514/574

(56) References Cited

PUBLICATIONS

Kiyoshi Ebihara et al., "Comparative effects of various organic acids on glucose–flattening activity in rats fed a glucose solution." *Nutr. Rep. int.* (1989), 40(5), pp. 1041–1047.
Database WPI, Section Ch., Week 199414. Derwent Publications Ltd., London; An 1994–114217. XP002123541 & JP 06 062798 A(Nakano Sumise KK), Mar. 8, 1994.
Database WPI, Section Ch., Week 198637. Derwent Publications Ltd., London; An 1986–242355. XP00212544 & JP 61 171417 A (Wakunaga Seiyaku KK), Aug. 2, 1986.
Michael J. MacDonald et al., "Glyceraldehyde phosphate and methyl esters of succinic acid. Two 'new' potent insulin secretagogues." *Diabetes* (1988), 37(7), pp. 997–999. XP0021235335.
Andre E. Lambert et al., "Organ culture of fetal rat pancreas. II. Insulin release induced by amino and organic acids, by hormonal peptides, by cationic alterations of the medium, and by other agents." *Biochim. Biophys. Acta* (1969), 184(3), pp. 540–543. XP002123536.
Willy Malaisse, "Insulinotropic Nutrient Esters." *Drugs of the Future*, vol. 23, No. 11, 1998, pp. 1205–1216. XP002123537.
Dzvonkevych and Guly, "Effects of Carboxylin, Acetate and the Acids of the Tricarboxylic Cycle on the Content of Glucose in Blood and Citric acid in Urine of Rabbits with Alloxan Diabetes." *Ukr. Biokhim. Zh.*, vol. 46, No. 5, 1974, pp. 547–542. XP002123538.
R. Korec, "Succinic acid alkyl esters—new generic oral anti-diabetic agents in alloxan and STZ diabetic rats." *Diabetologia*, vol. 40, No. suppl. 1, 1997, p. A375. XP002123539.
Leclerq–Meyer and Malaisse, "Potentiation of GLP–1 Insulinotropic Action by a Nonglucidic Nutrient in the Pancreas of Diabetic GK Rats." *Biochemical and Molecular Medicine*, vol. 59, No. 1, 1996, pp. 87–90. XP002123540.

*Primary Examiner*—Phyllis G. Spivack
(74) *Attorney, Agent, or Firm*—Lackenbach Siegel LLP

(57) ABSTRACT

The invention relates to methods of treating insulin resistance in mammals, preferably in humans, which methods comprise administering to a mammal in need thereof an effective amounts of succinic acid or a pharmaceutically acceptable salts thereof.

23 Claims, No Drawings

METHOD OF TREATING INSULIN RESISTANCE

TECHNICAL FIELD

The present invention is in the field of medicine, particularly in the treatment of states of insulin resistance that can result from disorders such as dibetes mellitus and its chronic complications such as retinopathy, polyneuropathy, nephropathy, angiopathy; gestational diabetes mellitus; impaired glucose tolerance; obesity; aging; atherosclerosis; syndrome X; cardiovascular disease; AIDS; cancer; wasting/cachecxia; sepsis; trauma associated with burns; malnutrition; lupus and other autoimmune diseases; endocrine diseases; hyperuricemia; hyperlipidemia; dyslipidemia; polycystic ovary syndrome; or complications arising from athletic activity.

BACKGROUND ART

Succinic acid is the physiologically occurring substrate of succinate dehydrogenase in mammals that play a role in cellular respiration and energy metabolism.

Insulin resistance is a condition in which the tissues of the body fail to respond normally to insulin. DeFronzo, R. A. *J. Cardiomuscular Pharmacology* 20 (Suppl. 11): S1–S16 (1992). The insulin resistance manifesting itself in pathologically elevated endogenous insulin and glucose levels and predisposes to the development of a cluster of abnormalities, including some degree of impaired glucose tolerance, an increase in plasma triglycerides and low density lipoprotein cholesterol (LDL) levels, a decrease in high-density lipoprotein cholesterol (HDL) levels, high blood pressure, hyperuricemia, a decrease in plasma fibrinolytic activity, an increase in cardiovascular disease and atherosclerosis. Reaven, G. M. *Physiol-Rev.* 75(3): 473–86 (1995). The decompensated insulin resistance is widely believed to be an underlying cause of non-insulin dependent diabetes mellitus.

A method of treating insulin resistance is known which comprises administration of insulin. Yki-Jarvinen, H. et al. *N. Engl. J. Med.* 327: 1426–1433 (1992). However, a basic disorder in the case of insulin resistance lies in the glucose assimilation by peripheral tissues of a mammal body. In this connection, it is important to treat the glucose assimilation not by the administration of insulin or by the pharmaceutical drug stimulating the excretion of insulin, but by the mechanisms independent thereof. Haering H. U., Mehnert H., *Diabetologia* 36: 176–182 (1993).

Free fatty acids induce insulin resistance in human in a dose dependent fashion. Boden G. *Front. Biosci.* 3, d169–175 (1998); Boden G., *Diabetes* 46(1): 3–10 (1997). Lowering of plasma free fatty acid levels is accordingly effective in the treatment of insulin resistance in a mammal.

Surprisingly, it has now been found that administration of an effective amount of succinic acid or salt thereof to insulin resistant mammals is effective therapy for treating of insulin resistance. Lowering of plasma free fatty acid levels accompanies a lowering of pathologically elevated insulin and glucose levels that reflects an improving in insulin sensitivity. More surprisingly, this biological effect is a long-term, and the best results are achieved in the after-treatment period.

This result is unexpected to Japanese Patent No. 61171417 describing that dicarboxylic acids including succinic acid are useful as antidiabetics showing promoting action on insulin secretion. More recently, MacDonald et al. demonstrated contrary to Japanese Patent No. 61171417 data that unesterified succinate, the compound of the present invention, did not stimulate insulin release in pancreatic islets but only esters of succinic acid are potent insulin secretagogues. MacDonald, M. J., Fahien, L. A. *Diabetes* 37(7): 997–999 (1988). Moreover, promotion of insulin secretion are useful in treating insulin dependent diabetic mammals with low or no insulin secretion, while insulin resistant mammals including non-insulin dependent diabetic mammals are needed in decreasing of elevated insulin levels rather than promotion of insulin secretion.

The present invention shows for the first time that succinic acid or salt thereof is useful for treating of insulin resistance in mammals, particularly in humans afflicted with non-insulin dependent diabetes mellitus.

It is an object of the present invention to provide the use of succinic acid or a pharmaceutically acceptable salt thereof for the manufacture of medicament or nutritional supplement useful for treating insulin resistance in a mammal.

It is an object of the present invention to provide a method of treating insulin resistance in a mammal, comprising administering to the mammal in need thereof of an effective amount of succinic acid or a pharmaceutically acceptable salt thereof. Orally, or parenterally, or topically, or rectally, as a nutritional supplement or medicament.

DISCLOSURE OF INVENTION

The present invention provides a method of treating insulin resistance in a mammal, which comprises administering to a mammal in need thereof an effective amount of succinic acid or a pharmaceutically acceptable salt thereof. Insulin resistance in the mammal can be associated with disorders such as diabetes mellitus and its chronic complications such as retinopathy, polyneuropathy, nephropathy, angiopathy; or gestational diabetes mellitus; or impaired glucose tolerance; or obesity; or aging; or atherosclerosis; or syndrome X; or cardiovascular disease; or AIDS; or cancer; or wasting/cachecxia; or sepsis; or trauma associated with burns; or malnutrition; or lupus and other autoimmune diseases; or endocrine diseases; or hyperuricemia; or hyperlipidemia; or dyslipidemia; or polycystic ovary syndrome; or complications arising from athletic activity. More particularly, the present invention provides the method of treating insulin resistance in a human afflicted with non-insulin dependent diabetes mellitus. Succinic acid has the chemical structure given below:

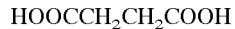

HOOCCH$_2$CH$_2$COOH

The pharmaceutically acceptable salt of the succinic acid is prepared by known methods from organic and inorganic bases. Such bases include, but are not limited to, nontoxic alkali metal and akaline earth bases, for example, calcium, lithium, sodium, and potassium hydroxide; ammonium hydroxide and nontoxic organic bases, such as triethylamine, butylamine, diethanolamine, triethanolamine and 2-ethyl-6-methyl-3-hydroxypyridine.

The succinic acid or a pharmaceutically acceptable salt thereof is preferably administered orally in the method of this invention. The succinic acid or a pharmaceutically acceptable salt thereof may also be administered by a variety of other routes such as parenterally, e.g. intravenously, subcutaneously, intramuscularly,; topically or rectally. Preferably, the succinic acid or pharmaceutically acceptable salt thereof is administered for a period of 1 day or longer; more preferably for a period of 3 to 7 days. The effective amount of succinic acid or a pharmaceutically acceptable salt thereof for use in the method of this invention is preferably from 0.1 milligram to 50 milligrams per day per kilogram of body weight of the mammalian subject, more preferably from 1 mg to 20 mg per day per kilogram of body weight of the mammalian subject.

Treating, as used herein, describes the managment and care of a mammal for the purpose of combating the disease, condition, or disorder and includes the administration of succinic acid or a pharmaceutically acceptable salt thereof to prevent the onset of the symptoms or complications, alleviating the symptoms or complications, or eliminating the disease, condition, or disorder. Treating of insulin resistance in a mammal includes increasing insulin sensitivity manifesting itself in a lowering of free fatty acid, insulin and glucose levels.

Also provided according to the present invention is the use of succinic acid or a pharmaceutically acceptable salt thereof for the manufacture of a medicament or nutritional supplement useful for treating insulin resistance in a mammal. Preferably, mammal is a human.

The medicaments or nutritional supplements of the invention are prepared by known procedures using well-known ingredients. In making the medicaments or nutritional supplements, the active ingredients will usually be mixed with a carrier, or diluted by a carrier, or enclosed within a carrier, and may be in the form of a capsule, tablet, paper or other container. When the carrier serves as a diluent, it may be a solid, semisolid, or liquid material which acts as a vehicle, excipient, or medium for the active ingredient. The nutritional supplements can be in the form of tablets, pills, powders, elixirs, suspensions, emulsions, solutions, syrups, soft and hard gelatin capsules. The medicaments can be in the form of tablets, pills, powders, elixirs, suspensions, emulsions, solutions, syrups, soft and hard gelatin capsules, aerosoles, suppositories, sterile injectable solutions, and sterile packaged powders.

Some examples of suitable carriers, diluents, and excipients include lactose, dextrose, sorbitol, mannitol, calcium phosphate, alginates, gelatin, calcium silicate, microcrystalline cellulose, polyvinylpyrrolidone, cellulose, water syrup, methyl cellulose, methyl and propyl hydroxybenzoates, talc, magnesium stearate; stearic acid, and mineral oil. The medicaments or nutritional supplements can additionally include lubricating agents, wetting agents, emulsifying and suspending agents, preserving agents, sweetening agents, or flavoring agents.

Preferably the medicament or nutritional supplement of the invention is in a dosage form and can be administrated orally, or parenterally, or topically, or rectally.

The medicament or nutritional supplement of the invention can be used advantageously in combination with antidiabetic drugs, particularly with insulin.

The following examples are presented to demonstrate the invention. The examples are illustrative only and are not intended to limit the scope of the invention in any way.

EXAMPLE 1

This example shows that administering an effective amount of succinic acid disodium salt hexahydrate to streptozotocin-induced rats is effective in treating insulin resistance.

Animals. Male albino Wistar rats 8–10 weeks of age 200–250 grams of body weight were used. The rats were housed at the temperature of 18±21° C. on a 12 hour light-dark cycle. Rats were fed on a stock laboratory diet (59% carbohydrates; 17% protein; 3% fat; 21% minerals, water, cellulose) and allowed water ad libitum. The streptozotocin (Sigma, St. Louis, Mo., USA) solved in citrate buffer (0.05M, pH 5.5) was injected into tail vein of male albino Wistar rats in a dose of 35 mg per kg of animal body weight to induce decompensated insulin resistance. The rats with levels of glucose more than 14.0 mmol/l were used in the experiment one week after the streptozotocin injection.

Assays. Plasma free fatty acids levels were determined by enzymatic method with a commercially available kit (Waho Chemicals Gmbh, Neuss, Germany) with Multistat 3 centrifugal analyzer (Instrumentation Laboratories, Lexington, USA).

Serum glucose concentrations were determined by the glucose oxidase method with a kit (Lachema, Slov.) with glucose analyzer (Beckman, Fullerton, Calif., USA).

Plasma insulin concentrations were determined by a double-antibody radioimmunoassay kit (Kabi Pharmacia Diagnostics, Uppsala, Sweden) using a rat insulin standard (Novo Research Institute, Bagsvard, Denmark).

Plasma triglycerides and cholesterol concentrations in High Density Lipoprotein (HDL) and Low Density Lipoprotein (LDL) were determined by enzymatic methods with kits (Boeringher Mannheim, Mannheim, Germany) with Multistat 3 F/LS apparatus (Instrumentation Laboratories, Lexington, USA).

Procedure. Streptozotocin-induced rats were assigned to two groups: a control rats (six rats) and experimental rats (fifteen rats). Experimental rats received daily injection (subcutaneously, 0.5 ml at 09.00 h) of water solution of succinic acid disodium salt hexahydrate in a dose of 5 mg per kg of body weight for period of 7 days.

Plasma free fatty acid levels (FFA), plasma Insulin levels and serum glucose levels were measured in rats by tail clipping method at zero day (before treatment), at third, fifth and seventh days (treatment period), and at tenth, fifteen, twentieth, twenty fifth and thirtieth days (after-treatment period).

The results are demonstrated in Table 1 through 3.

TABLE 1

Mean plasma FFA levels in experimental rats in comparison with control rats.

| | | FFA, mmol/l | |
| --- | --- | --- | --- |
| | Days | Control rats | Experimental rats |
| Before treatment | 0 | 0.31 ± 0.02 | 0.35 ± 0.03 |
| Treatment | 3 | 0.30 ± 0.03 | 0.32 ± 0.04 |
| period | 5 | 0.31 ± 0.05 | 0.25 ± 0.06 |
| | 7 | 0.29 ± 0.04 | 0.18 ± 0.05 |
| After- | 10 | 0.31 ± 0.03 | 0.20 ± 0.06 |
| treatment | 15 | 0.28 ± 0.02 | 0.15 ± 0.03 |
| period | 20 | exitus | 0.10 ± 0.05* |
| | 25 | letalis | 0.11 ± 0.04* |
| | 30 | | 0.13 ± 0.04* |

*Denotes statistically significant means ($p < 0.05$).

TABLE 2

Mean plasma insulin and serum glucose levels in experimental rats.

| | Days | Insulin, ng/ml | Glucose, mmol/l |
| --- | --- | --- | --- |
| Before treatment | 0 | 11.0 ± 0.7 | 15.7 ± 2.6 |
| Treatment | 3 | 10.2 ± 1.1 | 15.8 ± 3.1 |
| period | 5 | 7.4 ± 0.8 | 13.0 ± 2.4 |
| | 7 | 4.2 ± 0.7 | 10.0 ± 1.2 |
| After-treatment | 10 | 3.1 ± 0.8 | 10.1 ± 2.0* |
| period | 15 | 2.4 ± 0.4 | 8.1 ± 1.1 |

TABLE 2-continued

Mean plasma insulin and serum glucose levels in experimental rats.

| Days | Insulin, ng/ml | Glucose, mmol/l |
|---|---|---|
| 20 | 2.1 ± 0.4 | 6.6 ± 0.8 |
| 25 | 2.0 ± 0.3 | 5.7 ± 0.5* |
| 30 | 2.1 ± 0.3 | 5.4 ± 0.7 |

*Denotes statistically significant means (p < 0.05).

TABLE 3

Mean plasma insulin and serum glucose levels in control rats.

| | Days | Insulin, ng/ml | Glucose, mmol/l |
|---|---|---|---|
| Before treatment | 0 | 10.3 ± 1.2 | 15.7 ± 2.6 |
| Treatment period | 3 | 9.6 ± 1.4 | 15.1 ± 1.8 |
| | 5 | 9.0 ± 0.8 | 14.7 ± 1.4 |
| | 7 | 7.0 ± 1.3 | 13.3 ± 1.4 |
| After-treatment period | 10 | 9.3 ± 0.8 | 14.1 ± 0.6 |
| | 15 | 10.4 ± 1.4 | 13.0 ± 0.8 |
| | 20 | exitus | exitus |
| | 25 | letalis | letalis |
| | 30 | | |

The data of the Table 1 through 3 demonstrate that treating insulin resistant rats by the effective amount of succinic acid disodium salt hexahydrate causes a significant improving in insulin sensitivity in comparison with control insulin resistant rats that manifests itself in lowering of pathologically elevated plasma free fatty acid levels, plasma insulin and serum glucose levels. Maximal efficacy of the treating is achieved in the after-treatment period.

Administration of succinic acid disodium salt hexahydrate to healthy rats causes no changes in plasma free fatty acid levels (0.08±0.03 mmol/l), in serum glucose (4.8±0.4 mmol/l) and plasma insulin levels (3.4±0.6 ng/ml) during thirty days of the experiment analogous to described above.

EXAMPLE 2

This example shows that administering to non-insulin dependent diabetic humans an effective amount of succinic acid is an effective therapy for treating insulin resistance.

Patients. Twelve non-insulin dependent diabetic humans were studied. Non-insulin Dependent Diabetes Mellitus (NIDDM) was diagnosed in the humans according to the World Health Organisation criteria and had been presented for minimum 5 years. The NIDDM humans were metabolically stable and had glucose levels more than 12.8 mmol/l. Six patients were taking oral sulphonylurea hypoglicemic drug glibenclamide (rec. INN). None of the humans were undergoing hypolipidemic therapy. The humans had no additive metabolic disorders.

The following table summarizes the characteristics of the humans:

| | Mean ± SD | |
|---|---|---|
| Number of humans | 12 | |
| Age, years | 65 ± 3 | |
| Gender, men/women | 4/8 | |
| BMI | 25.1 ± 0.8 | kg/m² |
| Fasting plasma glucose | 13.7 ± 0.6 | mmol/l |
| Plasma FFA | 0.240 ± 0.044 | mmol/l |
| Plasma insulin | 140 ± 23 | pmol/l |
| Plasma LDL cholesterol | 4.8 ± 0.3 | mmol/l |
| Plasma HDL cholesterol | 0.6 ± 0.4 | mmol/l |
| Total cholesterol | 6.8 ± 0.4 | mmol/l |
| Plasma triglycerides | 2.7 ± 0.3 | mmol/l |
| Glycated hemoglobin | 11.4 ± 1.2 | % |

Assays. Assays were used as described in the example 1 of the invention. Plasma insulin concentrations were determined by a double-antibody radioimmunoassay kit (Kabi Pharmacia Diagnostics, Uppsala, Sweden).

Procedure. Pharmaceutical grade succinic acid in a unit dosage form of 100 mg per gelatin capsule was used. All patients received succinic acid orally in daily dose of 200 mg to 400 mg per day for period of 3 to 7 days.

Plasma free fatty acid levels, insulin levels and serum glucose levels, plasma high density lipoprotein cholesterol (HDL-cholesterol), low density lipoprotein cholesterol (LDL-cholesterol) and triglycerides were measured in humans at zero day (before treatment), at third and fifth days (treatment period), and at tenth, fifteen twentieth, twenty fifth thirtieth and fortieth days (after-treatment period). The resulted are demonstrated in Tables 4 through 6.

TABLE 4

Mean plasma FFA levels in NIDDM humans treated by succinic acid

| | Days | FFA, mmol/l |
|---|---|---|
| Before treatment | 0 | 0.240 ± 0.044 |
| Treatment period | 3 | 0.250 ± 0.071 |
| | 5 | 0.195 ± 0.064 |
| After-treatment period | 10 | 0.184 ± 0.035 |
| | 15 | 0.157 ± 0.032 |
| | 20 | 0.161 ± 0.034 |
| | 25 | 0.113 ± 0.046* |
| | 30 | 0.086 ± 0.035* |
| | 40 | 0.100 ± 0.022 |

*Denotes statistically significant means (p < 0.05).

TABLE 5

Mean plasma insulin and serum glucose levels in NIDDM humans treated by succinic acid.

| | Days | Insulin, pmol/l | Glucose, mmol/l |
|---|---|---|---|
| Before treatment | 0 | 140 ± 23 | 14.8 ± 1.4 |
| Treatment period | 3 | — | 14.5 ± 1.4 |
| | 5 | — | 14.9 ± 1.5 |
| After-treatment period | 10 | 134 ± 27 | 13.0 ± 2.0 |
| | 15 | — | 13.1 ± 0.8 |
| | 20 | 124 ± 17 | 11.0 ± 1.0 |
| | 25 | — | 9.4 ± 1.3 |
| | 30 | 118 ± 21 | 7.1 ± 0.6 |
| | 40 | 112 ± 14 | 5.8 ± 1.1 |

The data of the Tables 4 and 5 demonstrate that the treating of the non-insulin dependent diabetic humans by effective amount of succinic acid causes an improving in insulin sensitivity that manifests itself in lowering of free fatty acid levels, insulin and glucose levels. Maximal efficacy of the treating is achieved in the after-treatment period.

TABLE 6

Mean Plasma Low Density Lipoprotein cholesterol (LDL), High Density Lipoprotein cholesterol (HDL), and Triglycerides levels in NIDDM humans treated by succinic acid.

|  | Days | LDL, mmol/l | HDL, mmol/l | Triglycerides, mmol/l |
|---|---|---|---|---|
| Before treatment | 0 | 4.8 ± 0.3 | 0.6 ± 0.4 | 2.7 ± 0.3 |
| Treatment period | 3 | 4.9 ± 0.4 | 0.7 ± 0.2 | 2.8 ± 0.6 |
|  | 5 | 4.7 ± 0.2 | 0.8 ± 0.2 | 2.7 ± 0.3 |
| After treatment period | 10 | 4.3 ± 0.6 | 1.2 ± 0.4 | 2.5 ± 0.3 |
|  | 15 | 4.0 ± 0.3 | 1.2 ± 0.3 | 2.4 ± 0.4 |
|  | 20 | 3.5 ± 0.4 | 1.2 ± 0.4 | 1.8 ± 0.4 |
|  | 25 | 3.4 ± 0.3 | 1.3 ± 0.2* | 1.3 ± 0.2 |
|  | 30 | 3.4 ± 0.2 | 1.5 ± 0.2* | 1.1 ± 0.1* |
|  | 40 | 3.5 ± 0.4 | 1.3 ± 0.2 | 1.4 ± 0.2 |

*Denotes statistically significant means ($p < 0.05$).

The data of the Table 6 demonstrate that increasing of insulin sensitivity in non-insulin dependent diabetic humans treated by effective amount of succinic acid causes to reducing plasma triglycerides and low density lipoprotein cholesterol, and increasing plasma high density lipoprotein cholesterol, especially is in the after-treatment period.

Thus, the administration of succinic acid or salt thereof is an effective therapy for treating of insulin resistance.

We claim:

1. A method of treating insulin resistance in a mammal, which comprises administering to a mammal in need thereof an effective amount of succinic acid or a pharmaceutically acceptable salt thereof.

2. The method as claimed in claim 1 wherein the effective amount of succinic acid, or a pharmaceutically acceptable salt thereof, is 0.1 milligram to 50 milligrams per kilogram of body weight per day.

3. The method as claimed in claim 2 wherein the succinic acid or a pharmaceutically acceptable salt thereof is administered orally, or parenterally, or topically, or rectally.

4. The method as claimed in claim 2 wherein the succinic acid or a pharmaceutically acceptable salt thereof is administered for a period of 1 day or longer.

5. The method as claimed in claim 2 wherein the mammal is human.

6. The method as claimed in claim 5 wherein the human is a non-insulin dependent diabetic human.

7. The method as claimed in claim 1 wherein the effective amount of succinic acid or a pharmaceutically acceptable salt thereof is 1 milligram to 20 milligrams per kilogram of body weight per day.

8. The method as claimed in claim 7 wherein the succinic acid or a pharmaceutically acceptable salt thereof is administered orally, or parenterally, or topically, or rectally.

9. The method as claimed in claim 7 wherein the succinic acid or a pharmaceutically acceptable salt thereof is administered for a period of 1 day or longer.

10. The method as claimed in claim 7 wherein the mammal is human.

11. The method as claimed in claim 10 wherein the human is a non-insulin dependent diabetic human.

12. The method as claimed in claim 1 wherein the succinic acid or a pharmaceutically acceptable salt thereof is administered orally, or parenterally, or topically, or rectally.

13. The method as claimed in claim 12 wherein the succinic acid or a pharmaceutically acceptable salt thereof is administered for a period of 1 day or longer.

14. The method as claimed in claim 12 wherein the mammal is human.

15. The method as claimed in claim 14 wherein the human is a non-insulin dependent diabetic human.

16. The method as claimed in claim 1 wherein the succinic acid or a pharmaceutically acceptable salt thereof is administered for a period of 1 day or longer.

17. The method as claimed in claim 16 wherein the succinic acid or a pharmaceutically acceptable salt thereof is administered for a period of 3 to 7 days.

18. The method as claimed in claim 17 wherein the mammal is human.

19. The method as claimed in claim 18 wherein the human is a non-insulin dependent diabetic human.

20. The method as claimed in claim 16 wherein the mammal is human.

21. The method as claimed in claim 20 wherein the human is a non-insulin dependent diabetic human.

22. The method as claimed in claim 1 wherein the mammal is human.

23. The method as claimed in claim 22 wherein the human is a non-insulin dependent diabetic human.

* * * * *